United States Patent
Omote

(10) Patent No.: US 7,221,734 B2
(45) Date of Patent: May 22, 2007

(54) METHOD FOR X-RAY REFLECTANCE MEASUREMENT

(75) Inventor: Kazuhiko Omote, Akiruno (JP)

(73) Assignee: Rigaku Corporation, Tokyo (JP)

( * ) Notice: Subject to any disclaimer, the term of this patent is extended or adjusted under 35 U.S.C. 154(b) by 118 days.

(21) Appl. No.: 11/083,775

(22) Filed: Mar. 18, 2005

(65) Prior Publication Data

US 2005/0207532 A1   Sep. 22, 2005

(30) Foreign Application Priority Data

Mar. 22, 2004   (JP)   ............... 2004-081880

(51) Int. Cl.
*G01N 23/20* (2006.01)
(52) U.S. Cl. .............. 378/70; 378/84; 378/89
(58) Field of Classification Search ............. 378/70–90
See application file for complete search history.

(56) References Cited

FOREIGN PATENT DOCUMENTS

| JP | 10-38821 A | 2/1998 |
|---|---|---|
| JP | 11-237349 | 8/1999 |
| JP | 2004-37360 A | 2/2004 |

OTHER PUBLICATIONS

S. Kishimoto, et al., "A fast detector using stacked avalanche photodiodes for x-ray diffraction experiments with synchrotron radiation" Review of Scientific Instruments, vol. 69, No. 2, Feb. 1998, pp. 384-391, XP002333237.

Y. Hayasaki et al., "Measurement of resonant x-ray magnetic scattering from induced Cu polarizations in exchange-coupled Co/Cu multilayers." Journal of Physics: Condensed Matter, vol. 16, Mar. 12, 2004, pp. 1915-1925, XP002333238.

*Primary Examiner*—Edward J. Glick
*Assistant Examiner*—Jurie Yun
(74) *Attorney, Agent, or Firm*—Frishauf, Holtz, Goodman & Chick, P.C.

(57) ABSTRACT

An X-ray reflectance is measured with the use of an X-ray detector, which is not less than $10^7$ cps in upper-limit counting rate and is not more than twenty cps in noise level, under the condition that a measuring time length per interval of scattering angle $2\theta$ is not more than fifty milliseconds, so that the measurement of one reflectance curve is completed in a short time as several seconds. In another aspect of the invention, the X-ray detector used is not less than $10^7$ cps in upper-limit counting rate and is not more than 0.01 cps in noise level, and the measuring time length per interval is not less than a hundred seconds, so that the X-ray reflectance curve is obtained with not less than a nine-digit dynamic range. The X-ray detector may be an avalanche photo diode.

8 Claims, 11 Drawing Sheets

FIG. 7A

Table 1   2θ scanning in $Ta_2O_5$/Si measurement

| | Measuring interval in 2θ (deg) | Measuring time length per interval (msec) | Scanning speed in 2θ (deg/sec) | Time required for one degree (sec) |
|---|---|---|---|---|
| Measurement 1 | 0.01 | 500 | 0.02 | 50 |
| Measurement 2 | 0.01 | 100 | 0.1 | 10 |
| Measurement 3 | 0.02 | 50 | 0.4 | 2.5 |
| Measurement 4 | 0.02 | 20 | 1 | 1 |

FIG. 7B

Table 2  2θ scanning in TiN/Si measurement

| | Measuring interval in 2θ (deg) | Measuring time length per interval (msec) | Scanning speed of 2θ (deg/sec) | Time required for one degree (sec) |
|---|---|---|---|---|
| Measurement 1 | 0.01 | 1000 | 0.01 | 100 |
| Measurement 2 | 0.01 | 50 | 0.2 | 5 |
| Measurement 3 | 0.01 | 20 | 0.5 | 2 |
| Measurement 4 | 0.01 | 10 | 1 | 1 |

FIG. 9

Table 3

| Sample \ Result | Ta$_2$O$_5$/Si | | TiN/Si | |
|---|---|---|---|---|
| Measurement code | Measurement 1 | Measurement 4 | Measurement 1 | Measurement 4 |
| Measuring time length (msec) | 500 | 20 | 1000 | 10 |
| Scanning speed (deg/sec) | 0.02 | 1 | 0.01 | 1 |
| Film thickness (nm) | 9.54 | 9.56 | 4.935 | 4.904 |
| Surface roughness (nm) | 0.63 | 0.73 | 2.06 | 2.04 |
| Boundary roughness (nm) | 0.29 | 0.39 | 0.55 | 0.53 |

# METHOD FOR X-RAY REFLECTANCE MEASUREMENT

BACKGROUND OF THE INVENTION

1. Field of the Invention

The present invention relates to a method for measuring an X-ray reflectance in a short time with the use of an X-ray detector having a high upper-limit counting rate, and a method for measuring an X-ray reflectance with a high dynamic range with the use of an X-ray detector having a low noise level.

2. Description of the Related Art

It is known to measure an X-ray reflectance of a thin film and analyze the properties of the thin film, e.g., a film thickness, a density, a surface roughness and a boundary roughness, based on the measured data, as disclosed in Japanese patent publication No. 10-38821 A (1998), which will be referred to as the first publication.

An X-ray reflectance curve can be determined in a manner that a reflected X-ray intensity is measured with the scanning of the scattering angle 2θ in a range between zero to five degrees for instance. If a reflected X-ray intensity is measured at 0.01-degree intervals in 2θ and a measuring time length per interval is set to be one second, there is required, for the range between zero to five degrees, five-hundred measurement steps, the total time required for the measurement being five-hundred seconds. As just described, it takes ordinarily around several minutes to determine one reflectance curve. An X-ray detector may be, for instance, a proportional counter or a scintillation counter.

Incidentally, the present invention is concerned with the use of an avalanche photo diode as an X-ray detector, the avalanche photo diode being abbreviated to "APD" hereinafter. An X-ray analytical apparatus using the APD as an X-ray detector is known and disclosed in, for instance, Japanese patent publication No. 2004-37360 A, which will be referred to as the second publication.

The second publication discloses that a fluorescent X-ray holography detection system uses the APD having a high counting rate so as to complete the measurement in a shorter time than before. It says in the second publication that since the counting rate of the APD is high as not less than $10^6$ cps, the time required for detecting an X-ray at any measuring point is not more than one second and the total measuring time is reduced from around two months to around several hours when the fluorescent X-ray intensity is measured even under many angular conditions.

It is sometimes the case, as in the process of semiconductor device manufacturing, that the X-ray reflectance measurement must be carried out for many measuring positions on a single substrate to analyze the properties of the thin film, such as a film thickness for instance, for respective measuring positions. Assuming that it takes several minutes for the measurement at one measuring position, it takes several dozen minutes for the measurements at ten measuring positions. If the time required for the measurement at one measuring position is reduced to several seconds, it would take mere several dozen seconds for the measurements at ten measuring positions, completing the total measurement process in a very short time. Such a short-time measurement has been desired.

On the other hand, in the field of the X-ray analysis, it is known to use the APD having a high counting rate to reduce the measuring time as disclosed in the second publication. The second publication is, however, concerned with the special use as detecting very small fluorescent X-ray hologram signal, in which the long-term measuring time of around two months with the use of the ordinary detector has been reduced to the several hours with the use of the APD. It is noted that, even using the APD, there is needed around one second for one step of the X-ray intensity measurement in the fluorescent X-ray hologram. On the contrary, in a measurement process in which the total process is completed in around several minutes with the use of the ordinary detector, such as the X-ray reflectance measurement, one measurement step at one scattering angle 2θ is completed in a short time as around one second inherently. It has been unknown to attempt to make such a measuring time further shorter. Besides, since the X-ray reflectance measurement often requires a five-digit dynamic range or over, it would be necessary to insert or remove an absorption plate in the middle of the measurement operation in the case of using the ordinary proportional counter or the scintillation counter having an upper-limit counting rate of not more than $10^6$ cps, the insertion or removable of the absorption plate being an obstacle to the reduction of the measuring time.

On the contrary, it is sometimes desired to measure a high-accuracy X-ray reflectance curve with a high dynamic range. Since the ordinary method uses the proportional counter or the scintillation counter as an X-ray detector, it is impossible to measure a weak X-ray intensity because of the inherent noise level of the X-ray detector and thus it is impossible to carry out the reflectance measurement with a high dynamic range.

SUMMARY OF THE INVENTION

It is an object of the present invention to provide a method for X-ray reflectance measurement which can complete the measurement in a short time as around several seconds.

It is another object of the present invention to provide a method for X-ray reflectance measurement which can obtain a high-accuracy reflectance curve with a high dynamic range.

The present invention is characterized in that an X-ray reflectance is measured with the use of an X-ray detector having a high counting rate. The first aspect of the present invention has the feature that a desired dynamic range is assured even when the measuring time length per interval is very short. The second aspect of the present invention has the feature that an X-ray reflectance curve data is obtained with an extremely high dynamic range with the use of an X-ray detector having a very low noise level if the measuring time length per interval is set to be long enough.

A method for X-ray reflectance measurement according the first aspect of the present invention is characterized in that there is prepared an X-ray detector which is not less than $10^7$ cps in upper-limit counting rate and is not more than twenty cps in noise level converted to the counting rate, and an X-ray reflectance is measured with the use of the X-ray detector under the condition that a measuring time length per interval of a scattering angle 2θ is not more than fifty milliseconds. The X-ray detector having such a property may be the APD. It is noted that cps as the unit of the counting rate suggests count per second.

Values of the measured X-ray reflectance remarkably vary with the scattering angle 2θ and the dynamic range for the values often becomes around a five-digit number or over. It is important, for measuring such an X-ray reflectance in a very short time as several seconds for instance, to carry out the measurement at one burst with the 2θ scanning only, without the insertion or removal of an absorption plate in the middle of the measurement operation. Accordingly, the measurement should be carried out with a high dynamic range and therefore there is required an X-ray detector having an upper-limit counting rate of not less than $10^7$ cps. Assuming that the measuring time length at any interval of the scattering angle 2θ is ten milliseconds for instance, it is required, for detecting one-count X-ray photon during the measuring time length, that an X-ray having an intensity of more than a hundred cps must be incident on the X-ray detector, the hundred cps having been calculated by the division of one count by ten milliseconds. In other words, it is impossible to detect an X-ray having an intensity of not more than a hundred cps in the measuring time length of ten milliseconds, the hundred cps being defined as the lower-limit counting rate for the ten-millisecond measuring time length. If the upper-limit counting rate of the X-ray detector is high as not less than $10^7$ cps, a $10^5$ dynamic range, i.e., five-digit dynamic range, can be ensured even in the very short measuring time length as the ten milliseconds, noting that the dynamic range is defined as a ratio of the upper-limit counting rate to the lower-limit counting rate and the $10^5$ dynamic range has been calculated by the division of the $10^7$ cps by the hundred cps. If the upper-limit counting rate is higher as $10^8$ cps, a six-digit dynamic range is ensured. If the upper-limit counting rate is further higher as $10^9$ cps, a seven-digit dynamic range is ensured.

On the other hand, assuming that the inherent noise level of the X-ray detector is not less than a hundred cps, it is impossible to detect the hundred-cps intensity which corresponds to the lower-limit counting rate for the ten-millisecond measuring time length, because it is hidden in the noise level. Accordingly, the noise level of the X-ray detector should be not more than the hundred cps for the accurate detection of the X-ray intensity with the ten-millisecond measuring time length.

The above-mentioned first aspect of the present invention focuses on the reduction of the measuring time length per interval, which is set to be not more than fifty milliseconds, so that even when the measurement is carried out at 0.01-degree intervals in scattering angle 2θ, a five-second term is enough for the measurement per degree. When at 0.02-degree intervals, a two-point-five-second term is enough per degree. In the latter case, a seven-point-five-second term is enough as the total time for measuring a reflectance curve in a range between zero to three degrees in scattering angle 2θ.

When the measuring time length per interval is set to be fifty milliseconds, the lower-limit counting rate becomes twenty cps, namely, it is impossible to detect an X-ray intensity of not more than twenty cps. Accordingly, there is no problem if the inherent noise level of the X-ray detector is not more than twenty cps. On the other hand, it is noted that the upper-limit counting rate of the X-ray detector is not less than $10^7$ cps. Therefore, the measurable dynamic range is five times $10^5$, which has been calculated by the division of $10^7$ by twenty. Assuming that the measuring time length per interval is reduced to ten milliseconds, the lower-limit counting rate comes up to a hundred cps, still ensuring a five-digit measurable dynamic range.

It is preferable, for ensuring a desired dynamic range and reducing the measurement time, to set the measuring time length per interval to be one through fifty milliseconds, more preferably five through twenty milliseconds.

A method for X-ray reflectance measurement according the second aspect of the present invention is characterized in that there is prepared an X-ray detector which is not less than $10^7$ cps in upper-limit counting rate and is not more than 0.01 cps in noise level converted to the counting rate, and an X-ray reflectance is measured with the use of the X-ray detector under the condition that the maximum measuring time length per interval of scattering angle 2θ is not less than a hundred seconds. If the measuring time length per interval is set to be constant for any value of the scattering angle 2θ, the constant measuring time length corresponds to the maximum measuring time length, which is set to be not less than a hundred seconds in the second aspect. On the other hand, if the measuring time length per interval varies with the scattering angle 2θ, the maximum of the varying values of the measuring time length should be not less than a hundred seconds. Since the larger the scattering angle 2θ the smaller the reflected X-ray intensity, the variation of the measuring time length per interval should be in the condition that the maximum value of the measuring time length per interval appears at the largest value of the scattering angle 2θ. The X-ray detector may be the APD in the second aspect of the present invention too.

The above-mentioned second aspect of the present invention focuses on the high dynamic range for obtaining an X-ray reflectance curve and uses, for this purpose, an X-ray detector which is not less than $10^7$ cps in upper-limit counting rate and is not more than 0.01 cps in noise level converted to the counting rate. Assuming that an X-ray intensity can be detected down to the noise level, the lower-limit counting rate is coincide with the noise level, the dynamic range being not less than $10^9$. It should be noted, however, that since the lower-limit counting rate is also determined by the measuring time length per interval, it is important, for getting the most out of the above-mentioned low noise level, to reduce the lower-limit counting rate down to under the low noise level. Then, it is possible to carry out the reflectance measurement with a high dynamic range with making active use of the low noise level. The measuring time length per interval may be at least a value with which the lower-limit counting rate becomes equivalent to the noise level. Accordingly, the measuring time length per interval of not less than a hundred seconds is enough in the case of using an X-ray detector having a noise level of 0.01 cps. If it is intended, however, to measure a reflected X-ray intensity which is far above the noise level, the X-ray detection would not be disturbed by the noise level even when the measuring time length per interval is reduced to under a hundred seconds. Therefore, the above-mentioned limit of the hundred seconds counts for in the case of measuring a low intensity of the reflected X-ray near the noise level. Then, the second aspect of the present invention has the feature that the "maximum value" of the measuring time length per interval is not less than a hundred seconds. The maximum value should appear at the largest point in a range of the scattering angle 2θ in which one reflectance curve will be measured.

After all, the first aspect of the present invention has an advantage that an X-ray reflectance can be measured in a short time as around several seconds. Accordingly, when it is intended to measure the X-ray reflectance for many positions on the substrate, the total time required is remarkably reduced. The second aspect of the present invention has an advantage that an X-ray reflectance can be measured with an extremely high dynamic range as not less than $10^9$, enabling a high-accuracy analysis of the thin film properties.

BRIEF DESCRIPTION OF THE DRAWINGS

FIG. 7A shows table 1 indicating scanning conditions in the measurement shown in FIG. 6;

FIG. 7B shows tables 2 indicating scanning condition in the measurement shown in FIG. 8;

FIG. 9 shows table 3 indicating comparison of the results of analysis for the measurement data in a low-speed scanning and a high-speed scanning.

DETAILED DESCRIPTION OF THE PREFERRED EMBODIMENTS

Figure 1A:
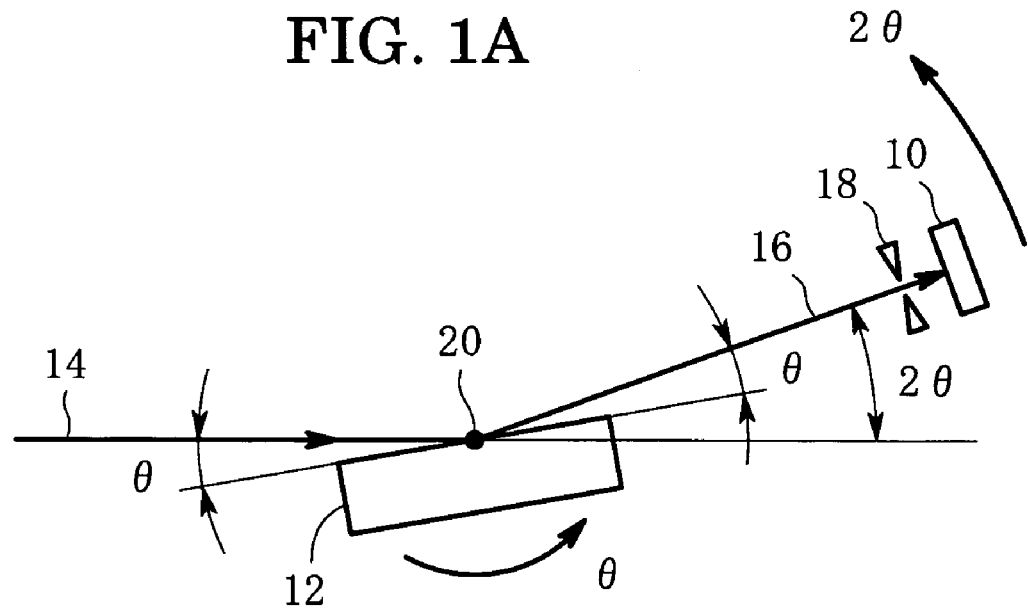
FIGS. 1A and 1B illustrate two arrangements of an optical system in a method for X-ray reflectance measurement according to the present invention.
Figure 1B:
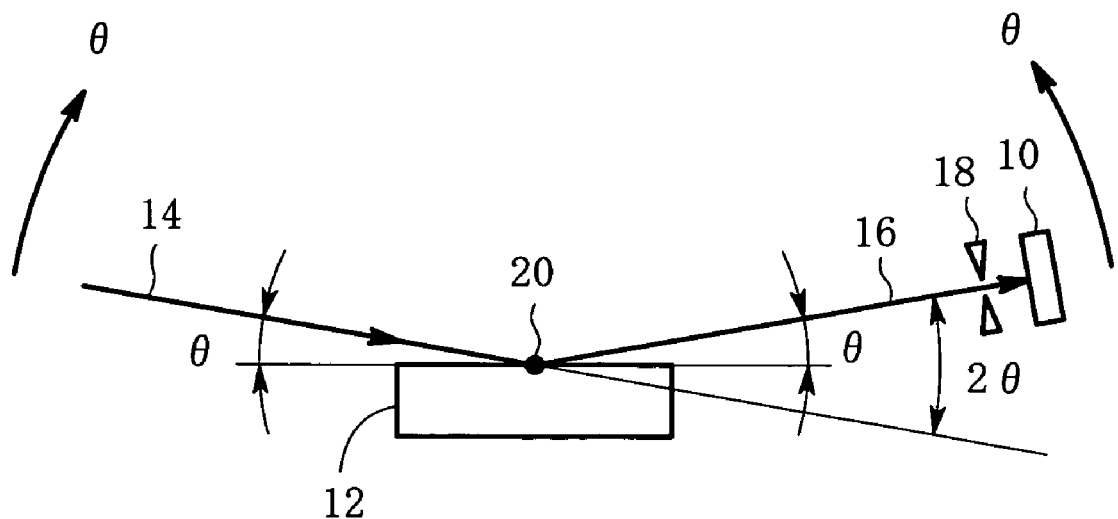

Embodiments of the present invention will now be described below with reference to the drawings. FIGS. 1A and 1B illustrate two arrangements of an optical system in a method for X-ray reflectance measurement according to the present invention. Referring to FIG. 1A, an X-ray detector 10 is an APD. An X-ray 14 is incident on the surface of a sample 12 at a small incident angle θ. An X-ray 16 reflected at the surface of the sample 12 passes through a receiving slit 18 and is detected by the APD 10, the slit 18 and the APD 10 being positioned at an outgoing angle θ from the surface of the sample 12. An assembly consisting of the receiving slit 18 and the APD 10 will be referred to as a receiving system hereinafter. An angle between the incident X-ray 14 and the reflected X-ray 16 is a scattering angle 2θ. The scattering angle 2θ is scanned in a manner that the sample 12 is rotated with a θ-rotation around the center 20 of a goniometer while the receiving system is rotated around the center 20 of the goniometer with a 2θ-rotation.

FIG. 1B illustrates another method for scanning the scattering angle 2θ. The sample 12 is set to be stationary relative to the space in FIG. 1B although the incident X-ray 14 in FIG. 1A is set to be stationary relative to the space. The scattering angle 2θ is scanned in FIG. 1B in a manner that the incident X-ray 14, i.e., an X-ray source, is rotated clockwise with a θ-rotation around the center 20 of the goniometer while the receiving system is rotated counterclockwise with a θ-rotation around the center 20 of the goniometer.

The method for X-ray reflectance measurement according to the present invention is applicable to any one of the scanning methods shown in FIGS. 1A and 1B. The first aspect of the present invention has the feature of a higher scanning speed than the ordinary X-ray reflectance measurement. Explaining an example, when it is intended to measure a reflected X-ray intensity at 0.02-degree intervals in 2θ with a measuring time length of twenty milliseconds per interval, a time required for the scanning from zero to five degrees in 2θ is short as five seconds. For realizing this measuring condition in the scanning method shown in FIG. 1A, the sample 12 should be turned at 0.01-degree intervals in the θ-rotation while the receiving system should be turned at 0.02-degree intervals in the 2θ-rotation. On the other hand, in the scanning method shown in FIG. 1B, the incident X-ray 14 should be turned at 0.01-degree intervals in the clockwise θ-rotation while the receiving system should be turned at 0.01-degree intervals in the counterclockwise θ-rotation. The 2θ-scanning may be carried out with any one of the continuous scanning, in which 2θ varies continuously during the detection of an X-ray intensity, and the stepwise scanning, in which 2θ does not vary during the detection of an X-ray intensity. It would be preferable, however, to use the continuous scanning for the first aspect of the present invention because the first aspect focuses on the short-time measurement.

Figure 2:
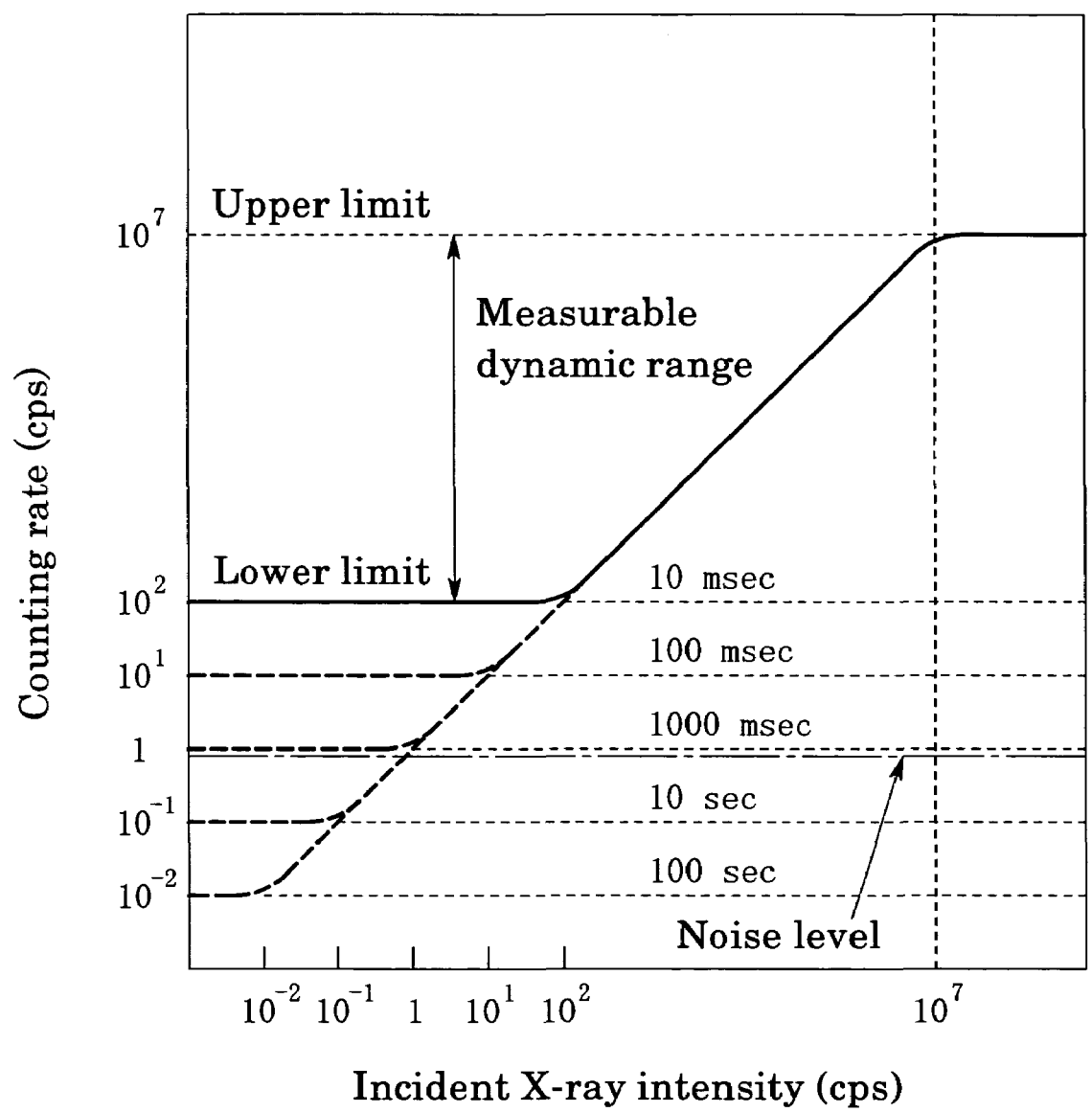
FIG. 2 is a graph showing the dynamic range of an X-ray detector.

The X-ray counting rate of the X-ray detector and the dynamic range of the measurement will now be described. FIG. 2 is a graph showing exemplarily a relationship between an actual intensity of an incident X-ray on the X-ray detector, measured in cps, and a counting rate which is the output of the X-ray detector, measured also in cps. When the incident X-ray intensity becomes very high, the counting rate comes to be saturated. The saturated counting rate is defined as the measurable upper-limit counting rate, which is represented by "upper limit" in FIG. 2, the value being $10^7$, ten to the seventh power, cps in this embodiment. On the other hand, when the incident X-ray intensity becomes very low, the measurement comes to be impossible, the lower limit being caused by the two factors. The first factor is the measuring time length per interval, and the second factor is the noise level of the X-ray detector. Explaining first the first factor, when the measuring time length per interval is very short as ten milliseconds for instance, an X-ray intensity of a hundred cps would be required for detecting at least one X-ray photon, the hundred cps having been calculated by the division of the one count by the ten milliseconds. If the X-ray intensity becomes lower than this level, one of the two cases occurs: one X-ray photon is counted during the measurement; and no X-ray photon is counted during the measurement. It would be impossible to determine the actual X-ray intensity in either case. Accordingly, the detector cannot detect an X-ray intensity lower than a hundred cps. This limit is represented by a horizontal line of ten milliseconds, 10 msec, in FIG. 2, the lower limit of the counting rate being a hundred cps in this example. Similarly, when the measuring time length per interval is set to be a hundred milliseconds, the lower-limit counting rate becomes ten cps. When the measuring time length per interval is set to be a thousand milliseconds, i.e., one second, the lower-limit counting rate becomes one cps.

The second factor will be described secondly. An X-ray detector has an inherent noise level, and therefore an incident X-ray intensity lower than the inherent noise level cannot be detected because it is hidden by the inherent noise level. The graph in FIG. 2 shows an embodiment in which the noise level is around one cps. An incident X-ray intensity lower than the noise level cannot be detected. After all, the larger of the two, the counting rate corresponding to the noise level and the lower-limit counting rate which is determined by the measuring time length per interval, becomes the actual lower-limit counting rate for the measurement in question. Explaining it referring to the graph in FIG. 2, when the measuring time length per interval is less than a thousand milliseconds, the lower-limit counting rate which is determined by the measuring time length per interval is used as the lower-limit counting rate for the measurement in question. On the contrary, when the measuring time length per interval is more than a thousand milliseconds, the counting rate corresponding to the noise level is used as the lower-limit counting rate, which comes not to depend on the measuring time length. The solid-line curve in FIG. 2 represents the counting rate when the measuring time length per interval is ten milliseconds, in which the upper limit is $10^7$ cps and the lower limit is a hundred cps, ensuring a five-digit measurable dynamic range.

Figure 3:
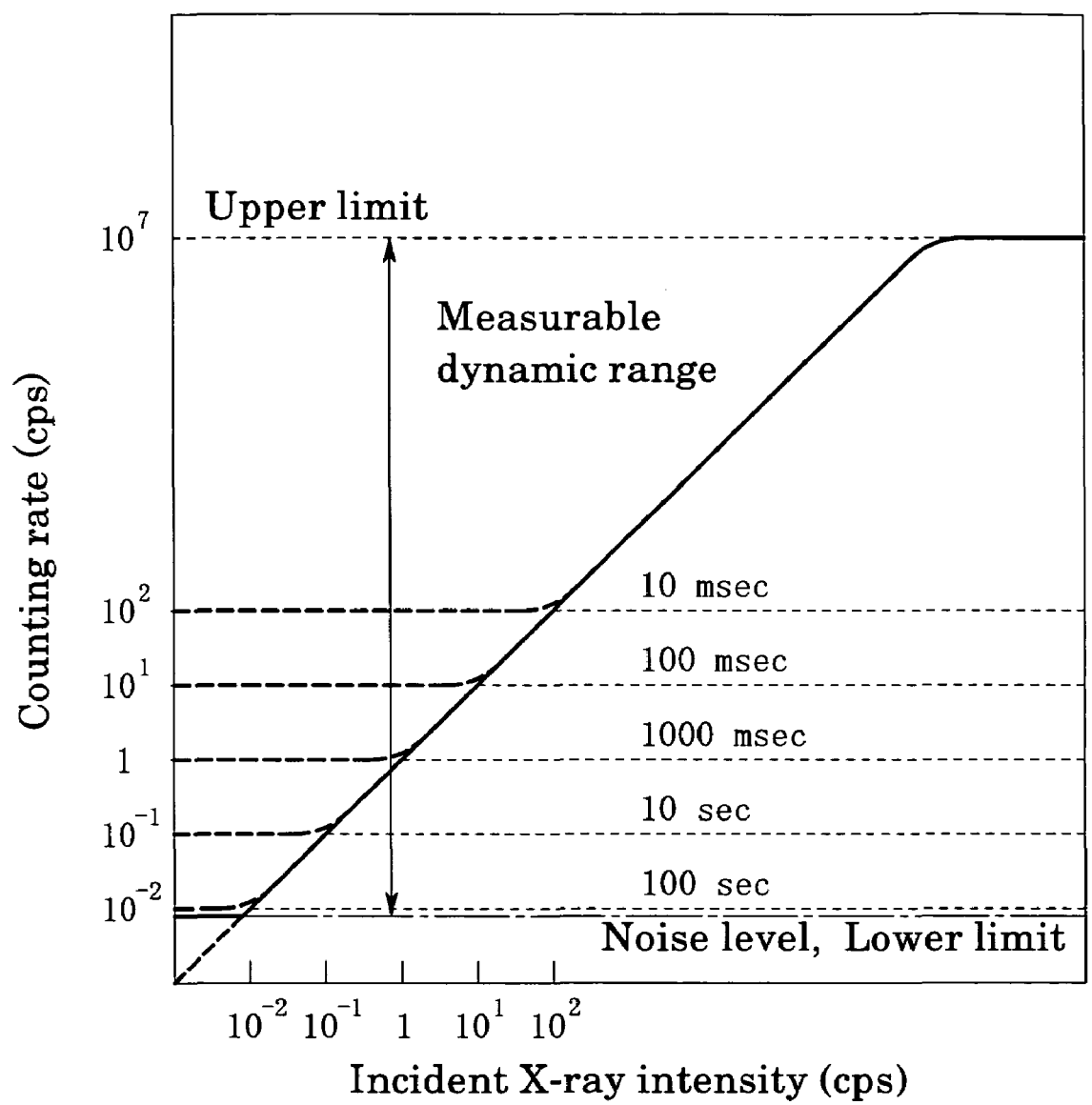
FIG. 3 is another graph showing the dynamic range of the X-ray detector.

FIG. 3 is a graph, similar to that in FIG. 2, for another X-ray detector having a very low noise level as around 0.01 cps, in which even if the measuring time length per interval is set to be considerably long, the counting rate determined by the measuring time length would not be lower than the noise level. The solid-line curve in FIG. 3 represents the counting rate when the measuring time length per interval is not less than a hundred seconds. When the measuring time length per interval runs up the hundred seconds, the lower-limit counting rate depending on the measuring time length becomes 0.01 cps at last, which is approximately equal to the noise level. As described above, when using the X-ray detector having the low noise level, the lower-limit counting rate can be reduced to a very low level by prolonging the measuring time length per interval, assuring a very high dynamic range. Stating the embodiment shown in FIG. 3, the upper limit is $10^7$ cps while the lower limit is 0.01 cps, and thus the measurable dynamic range becomes $10^9$.

The APD used in the embodiment is $10^8$ cps in upper limit and 0.002 cps in noise level. Accordingly, it is possible, with the APD, to shorten the measuring time length per interval to cut down the time required for the X-ray reflectance measurement to be several seconds, and alternatively it is possible to prolong the measuring time length per interval to observe an reflectance curve with a very high dynamic range.

Figure 4:
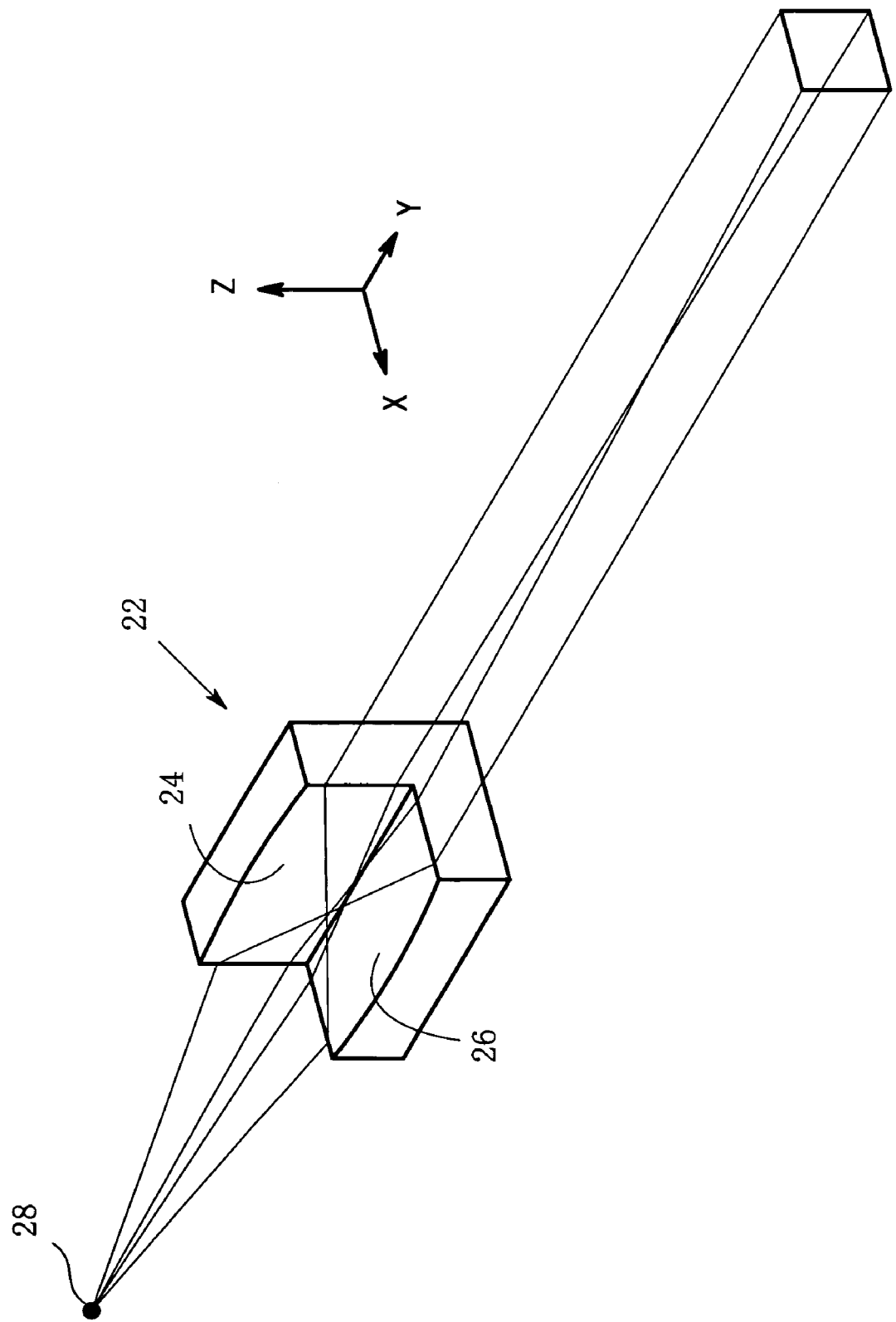
FIG. 4 is a perspective view of a multilayer mirror.

The incident X-ray will now be described. The present invention is characterized by the use of the X-ray detector having the upper-limit counting rate of not less than $10^7$, and thus the invention requires a high-intensity incident X-ray to make active use of the very high upper-limit counting rate. Then, the incident X-ray 14 in FIGS. 1A and 1B is made a high-intensity X-ray beam which is derived by using a multilayer mirror. FIG. 4 is a perspective view of the multilayer mirror used in the embodiment. The multilayer mirror 22 is comprised of the first mirror having the parabolic, first reflective surface 24 made of a synthetic multilayer film and the second mirror having the parabolic, second reflective surface 26 made of a synthetic multilayer film, the two mirrors being joined to each other on their lateral edges at an angle of around ninety degrees, so-called a side-by-side multilayer mirror. With this multilayer mirror 22, an X-ray beam emitted from the X-ray focus 28 of an X-ray tube, which is a divergent beam, can be collimated within an X-Y plane and also within a Y-Z plane. The X-ray which has been reflected first at the first reflective surface 24 is reflected at the second reflective surface 26 to go out. On the other hand, The X-ray which has been reflected first at the second reflective surface 26 is reflected at the first reflective surface 24 to go out. The first reflective surface 24 is for collimating the X-ray within the X-Y plane while the second reflective surface 26 is for collimating the X-ray within the Y-Z plane. The divergent X-ray beam from the X-ray focus 28 is collected and collimated by the parabolic surface so as to become a high-intensity parallel beam. The multilayer mirror 22 is arranged in the incident optical system so that the X-Y plane in FIG. 4 is positioned to be parallel to the drawing sheet of FIGS. 1A and 1B. When using a combination of the multilayer mirror 22 and the micro-focus X-ray source, the cross-sectional shape of the incident X-ray beam just before the irradiation of the sample becomes 1 mm times 0.1 mm for instance. The divergence angle of the X-ray beam within the X-Y plane and within the Y-Z plane is small as less than 0.03 degree.

Figure 5:
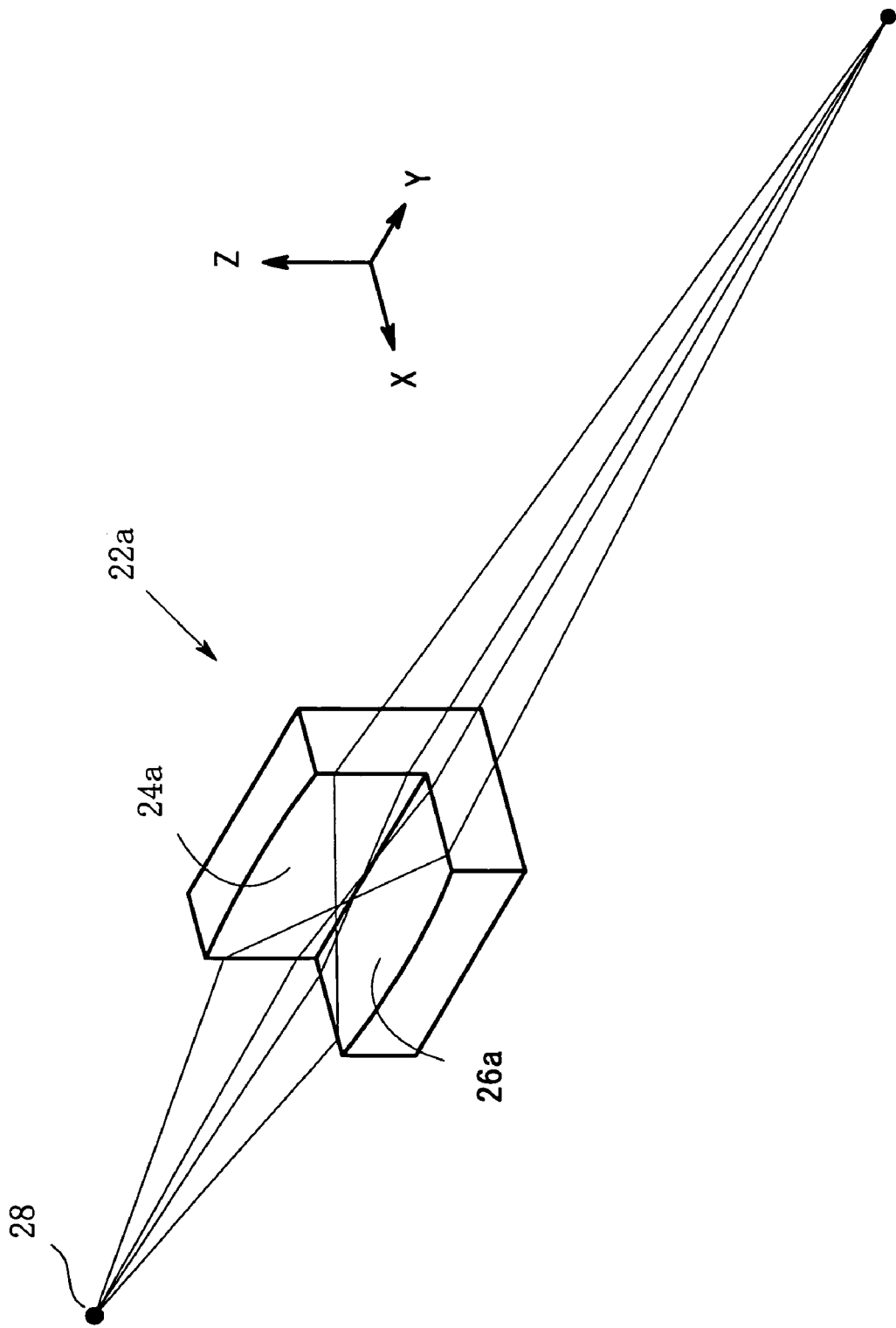
FIG. 5 is a perspective view of another multilayer mirror.

Another multilayer mirror will next be described. A multilayer mirror 22a shown in FIG. 5 has two elliptical reflective surfaces 24a and 26a. The X-ray beam from the multilayer mirror 22a becomes a focused beam which is focused on the surface of the sample within the X-Y plane and within the Y-Z plane. The multilayer mirror shown in FIG. 5 can make the incident X-ray intensity higher than that from the multilayer mirror shown in FIG. 4 although the divergence angle becomes larger. When using a combination of the multilayer mirror 22a and the micro-focus X-ray source, the cross-sectional shape of the incident X-ray beam just before the irradiation of the sample becomes 0.05 mm times 0.05 mm for instance. Assuming that the whole of the multilayer mirror is used under such a condition, the divergence angle becomes large as around one degree disadvantageously. It should be noted, however, that a slit can be used to limit the divergence angle to collimate the X-ray beam within the X-Y plane, so that an X-ray reflectance can be measured with around 0.05 degree in divergence angle.

Figure 6:
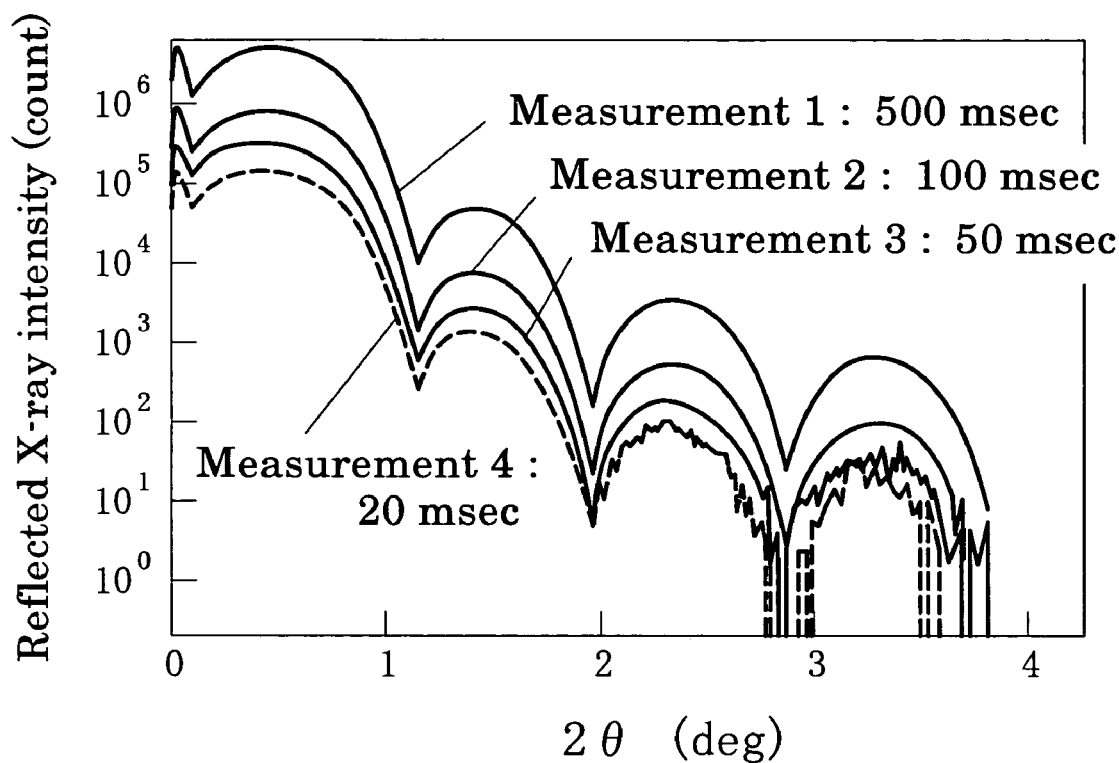
FIG. 6 is a graph showing X-ray reflectance curves for a $Ta_2O_5$ thin film.

Actual measurement examples will next be described. FIG. 6 is a graph showing X-ray reflectance curves for a $Ta_2O_5$, tantalum oxide, thin film deposited on a silicon substrate, measured by the method shown in FIG. 1A, a scattering angle $2\theta$ in abscissa while a reflected X-ray intensity represented by the number of counts in ordinate. The graph shows four kinds of reflectance curves for the different measuring time lengths, noting that the four curves would substantially overlap each other if the ordinate represents the counting rate, its unit being cps. Since the reflected X-ray intensity is represented by the number of counts, the shorter the measuring time length, i.e., the more the advance from the measurement 1 to the measurement 4, the smaller the reflected X-ray intensity by counts.

Measurement 1 represents the result measured at 0.01-degree intervals in $2\theta$ with 500 milliseconds in measuring time length per interval, the scanning speed of $2\theta$ being 0.02 degree per second accordingly. Measurement 2 is for 0.01-degree intervals, 100 milliseconds in measuring time length, and 0.1 degree per second in scanning speed. Measurement 3 is for 0.02-degree intervals, 50 milliseconds in measuring time length, and 0.4 degree per second in scanning speed. Measurement 4 is for 0.02-degree intervals, 20 milliseconds in measuring time length, and one degree per second in scanning speed. These values are shown together in Table 1 in FIG. 7A. The time required for one degree in $2\theta$ is 50 seconds in measurement 1, 10 seconds in measurement 2, 2.5 seconds in measurement 3 and one second in measurement 4. Assuming that the measuring range of the scattering angle $2\theta$ is between zero to five degrees, the time required for the range is 250 seconds in measurement 1, 50 seconds in measurement 2, 12.5 seconds in measurement 3 and five seconds in measurement 4. Since the first aspect of the present invention is characterized in that the measuring time length per interval of scattering angle $2\theta$ is set to be not more than fifty milliseconds, measurements 3 and 4 correspond to embodiments of the first aspect, measurements 1 and 2 being comparative examples. Referring to the graph shown in FIG. 6, measurements 1 and 2 clearly show the first to the fourth peaks of the interference patterns of the reflectance curves within a range between zero and four degrees in $2\theta$. Measurement 3 also clearly shows the first to the fourth peaks although the fourth peak includes some noise overlapping. Measurement 4 clearly shows the first to the third peaks although the third peak includes some noise overlapping. As long as such clear data can be observed, it is possible to analyze the thin film properties using reflectance curves such as measurements 3 and 4. It is noted that even measurement 4 would ensure an approximately five-digit dynamic range.

Figure 8:
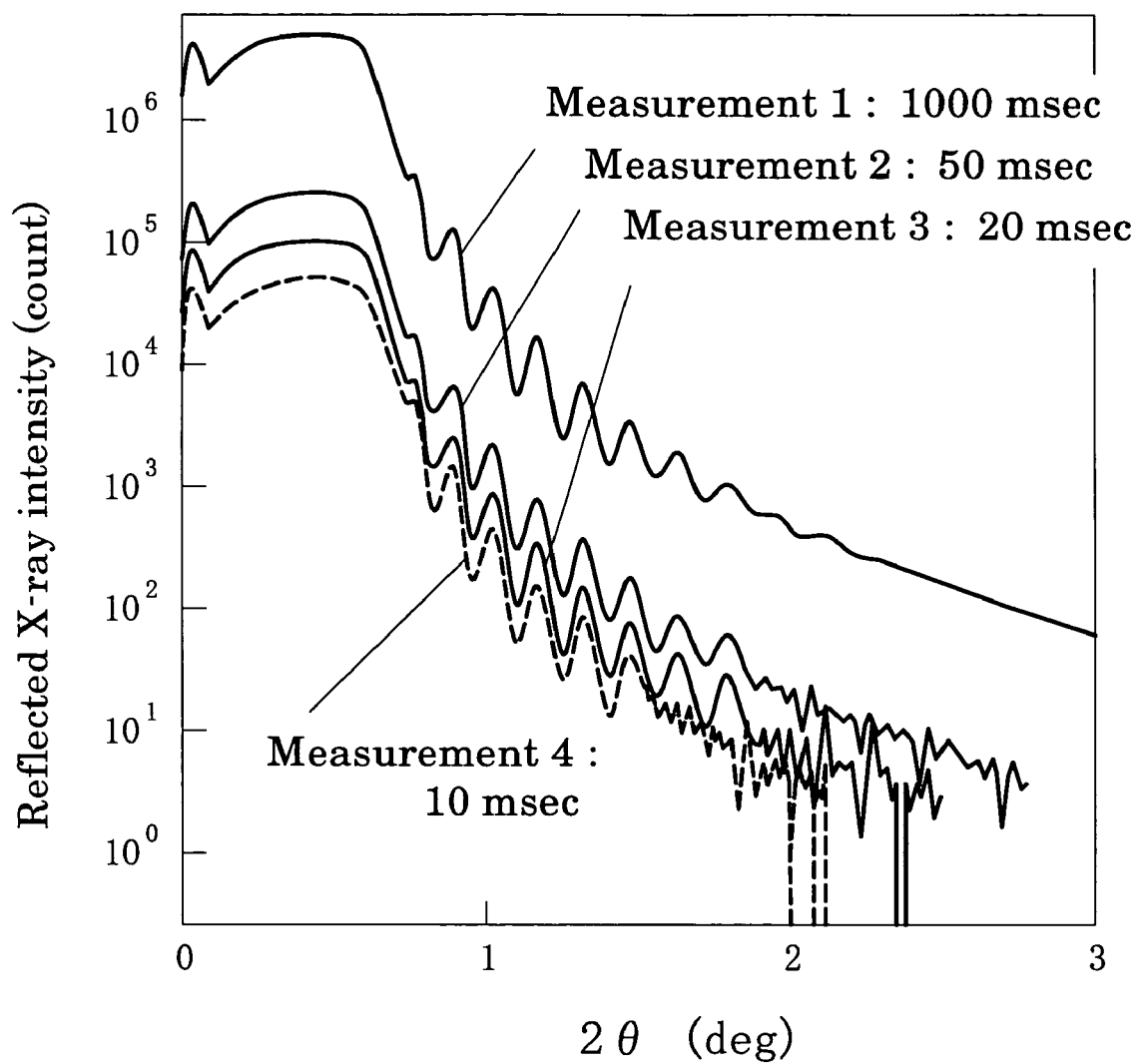
FIG. 8 is a graph showing X-ray reflectance curves for a TiN thin film.

Other measurement examples will next be described. FIG. 8 is a graph showing X-ray reflectance curves for a TiN, titanium nitride, thin film deposited on a silicon substrate, measured by the method shown in FIG. 1A, a scattering angle 2θ in abscissa while a reflected X-ray intensity represented by the number of counts in ordinate. The graph shows four kinds of reflectance curves for the different measuring time lengths, noting, similarly to the graph shown in FIG. 6, that the four curves would substantially overlap each other if the ordinate represents the counting rate, its unit being cps.

Measurement 1 represents the result measured at 0.01-degree intervals in 2θ with 1000 milliseconds in measuring time length per interval, the scanning speed of 2θ being 0.01 degree per second accordingly. Measurement 2 is for 0.01-degree intervals, 50 milliseconds in measuring time length, and 0.2 degree per second in scanning speed. Measurement 3 is for 0.01-degree intervals, 2θ milliseconds in measuring time length, and 0.5 degree per second in scanning speed. Measurement 4 is for 0.01-degree intervals, 10 milliseconds in measuring time length, and one degree per second in scanning speed. These values are shown together in Table 2 in FIG. 7B. The time required for one degree in 2θ is 100 seconds in measurement 1, five seconds in measurement 2, two seconds in measurement 3 and one second in measurement 4. Assuming that the measuring range of the scattering angle 2θ is between zero to three degrees, the time required for the range is 300 seconds in measurement 1, 15 seconds in measurement 2, six seconds in measurement 3 and three seconds in measurement 4. Since the first aspect of the present invention is characterized in that the measuring time length per interval of scattering angle 2θ is set to be not more than 50 milliseconds, measurements 2 through 4 correspond to embodiments of the first aspect, measurement 1 being a comparative example. Referring to FIG. 8, measurements 1 through 3 clearly show the oscillating curves of the interference pattern within a range up to near two degrees in 2θ. Measurement 4 clearly shows the oscillating curve of the interference pattern within a range up to near 1.5 degrees in 2θ. As long as such clear data can be observed, it is possible to analyze the thin film properties using these reflectance curves. It is noted that even measurement 4 would ensure an approximately four-digit dynamic range.

FIG. 9 shows table 3 which indicates comparison of the results of analysis derived from measurement 1, i.e., a low-speed scanning, and measurement 4, i.e., a high-speed scanning, for the measured data shown in FIGS. 6 and 8 respectively. Stating the measured data for the $Ta_2O_5$ thin film shown in FIG. 6, the properties determined based on the reflectance curve of measurement 1 are as follows: a film thickness is 9.54 nm, a surface roughness is 0.63 nm and a boundary roughness, i.e., a roughness of the boundary between the $Ta_2O_5$ thin film and the substrate, is 0.29 nm. On the other hand, the properties determined based on the reflectance curve of measurement 4 are as follows: a film thickness is 9.56 nm, a surface roughness is 0.73 nm and a boundary roughness is 0.39 nm. Comparing the film thickness values between the measurements 1 and 4, it is seen that the results of analysis are good consistent with each other. There is no substantial difference between the measurements 1 and 4 regarding the surface roughness and the boundary roughness too. Accordingly, it has been ascertained that even when analysis is carried out based on the reflectance curve observed in a high-speed measurement such as measurement 4, the result of analysis for the thin film properties would possess higher reliability.

Stating the measured data for the TiN thin film shown in FIG. 8, the properties determined based on the reflectance curve of measurement 1 are as follows: a film thickness is 4.935 nm, a surface roughness is 2.06 nm and a boundary roughness is 0.55 nm. On the other hand, the properties determined based on the reflectance curve of measurement 4 are as follows: a film thickness is 4.904 nm, a surface roughness is 2.04 nm and a boundary roughness is 0.53 nm. In the embodiment of the TiN thin film, the results of analysis are very good consistent with each other between the measurements 1 and 4 regarding the film thickness, the surface roughness and the boundary roughness respectively. Accordingly, it has been ascertained also for TiN that even when analysis is carried out based on the reflectance curve observed in a high-speed measurement such as measurement 4, the result of analysis for the thin film properties would possess higher reliability.

Figure 10:
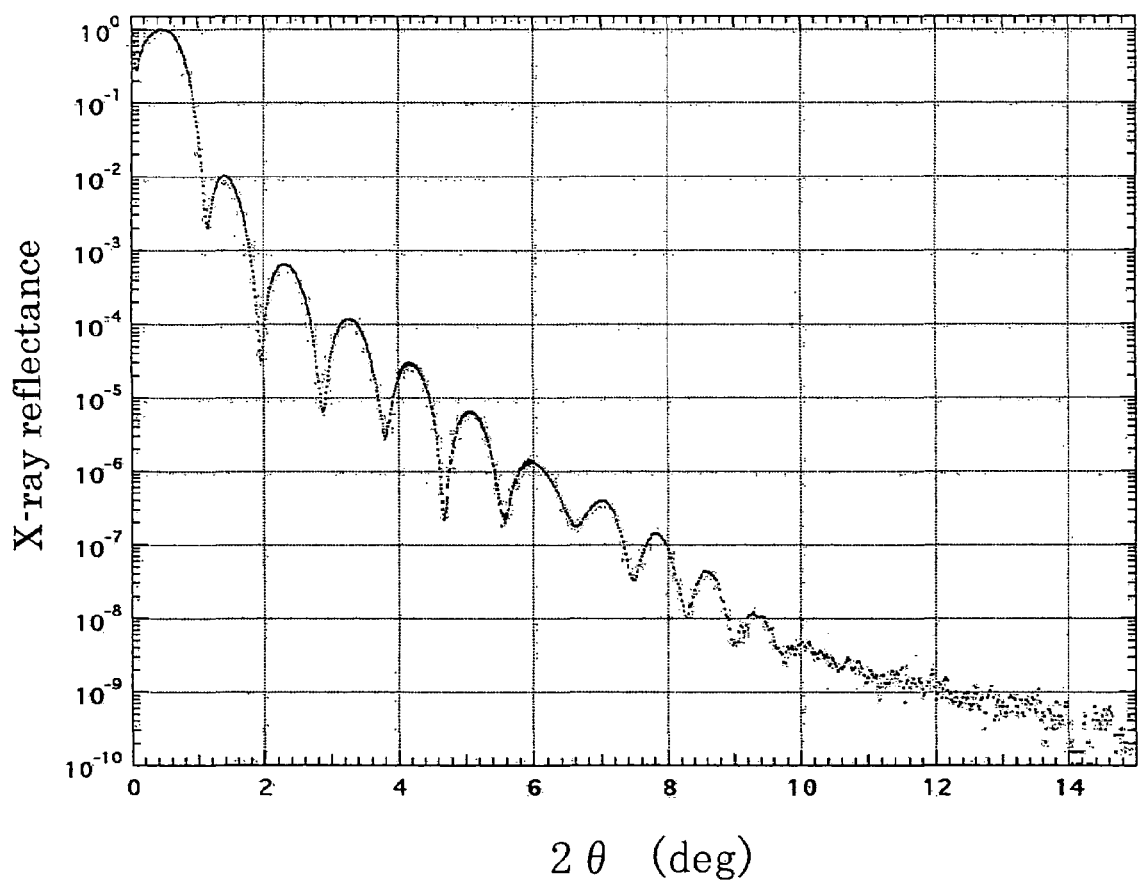
FIG. 10 is a graph showing an X-ray reflectance curve measured with an APD and with taking a sufficient time.

Embodiments of the second aspect of the present invention will next be described. FIG. 10 is a graph showing an X-ray reflectance curve measured with the use of an APD as an X-ray detector and with taking a sufficient time, a scattering angle 2θ in abscissa while a reflectance, i.e., a ratio of a reflected X-ray intensity to an incident X-ray intensity, in ordinate. A sample is a $Ta_2O_5$ thin film deposited on a silicon substrate and the thickness of the thin film is 10 nm. The reflectance is measured at 0.02-degree intervals in 2θ with ten seconds in measuring time length per interval within a range between zero to six degrees in 2θ, and at 0.02-degree intervals in 2θ with a hundred seconds in measuring time length per interval within a range between six to fourteen degrees in 2θ. The time required for a range between zero to six degrees is 3000 seconds while 40000 seconds for a range between six to fourteen degrees, the total time being 43000 seconds which is equal to around 12 hours. Thinking about a region in which 2θ is smaller, since the reflected X-ray intensity is higher, it is no problem, for good measurement, to shorten the measuring time length per interval because the X-ray intensity is higher than the lower-limit counting rate which is determined by the measuring time length. Thinking about another region in which 2θ is larger, since the reflected X-ray intensity becomes smaller, it is required to prolong the measuring time length per interval so as to reduce the lower-limit counting rate which is determined by the measuring time length. This embodiment selectively utilizes the above-mentioned two values of the measuring time length per interval, ten and a hundred seconds, to observe one reflectance curve, the maximum measuring time length per interval being the hundred seconds. Since the maximum measuring time length is set to be long enough, it is possible to carry out measurement with a high dynamic range with making active use of the low noise level.

It is seen from the graph shown in FIG. 10 that if the measuring time length per interval is set to be long enough, the ability of the APD can be brought out at the maximum, so that the periodic interference pattern clearly appears in a reflectance range down to under $10^{-8}$ ensuring a dynamic range of at least $10^9$.

What is claimed is:

1. A method for X-ray reflectance measurement is provided which comprises:
   (a) preparing an X-ray detector which is not less than $10^7$ cps in upper-limit counting rate and which is not more than twenty cps in noise level converted to a counting rate; and
   (b) measuring an X-ray reflectance using the X-ray detector under a condition that a measuring time length per interval of scattering angle $2^\theta$ is not more than fifty milliseconds.

2. A method according to claim 1, wherein the measuring time length per interval of scattering angle $2^\theta$ is within a range between two and twenty milliseconds.

3. A method according to claim 1, wherein the X-ray detector comprises an avalanche photo diode.

4. A method according to claim 1, wherein the X-ray reflectance is measured using an X-ray beam which has been reflected by a multilayer mirror having one of parabolic and elliptical reflective surfaces.

5. A method for X-ray reflectance measurement comprising:
  (a) preparing an X-ray detector which is not less than $10^7$ cps in upper-limit counting rate and which is not more than 0.01 cps in noise level converted to a counting rate; and
  (b) measuring an X-ray reflectance using the X-ray detector under a condition that a maximum measuring time length per interval of scattering angle $2^\theta$ is not less than a hundred seconds.

6. A method according to claim 5, wherein the X-ray detector comprises an avalanche photo diode.

7. A method according to claim 6, wherein the avalanche photo diode is not less than $10^8$ cps in upper-limit counting rate and is not more than 0.002 cps in noise level converted to the counting rate.

8. A method according to claim 5, wherein the X-ray reflectance is measured using an X-ray beam which has been reflected by a multilayer mirror having one of parabolic and elliptical reflective surfaces.

* * * * *